(12) United States Patent
Soltz

(10) Patent No.: US 7,049,590 B1
(45) Date of Patent: May 23, 2006

(54) CAPPING LAYER TO IMPEDE ATOM EJECTION

(75) Inventor: David Aitan Soltz, San Jose, CA (US)

(73) Assignee: KLA-Tencor Technologies Corporation, Milpitas, CA (US)

(*) Notice: Subject to any disclaimer, the term of this patent is extended or adjusted under 35 U.S.C. 154(b) by 0 days.

(21) Appl. No.: 10/977,620

(22) Filed: Oct. 28, 2004

(51) Int. Cl.
*G01N 23/223* (2006.01)

(52) U.S. Cl. .................. 250/310; 250/339; 378/46; 378/45

(58) Field of Classification Search ............. None
See application file for complete search history.

(56) References Cited

U.S. PATENT DOCUMENTS 4,937,094 A * 6/1990 Doehler et al. ............. 427/574
5,754,620 A * 5/1998 Hossain et al. ............... 378/45
6,787,773 B1 * 9/2004 Lee ............................. 250/311

\* cited by examiner

*Primary Examiner*—Nikita Wells
*Assistant Examiner*—Zia R. Hashmi
(74) *Attorney, Agent, or Firm*—Luedeka, Neely & Graham, P.C.

(57) ABSTRACT

A method of reducing atom ejection from a sample during electron beam bombardment. An electron beam is directed through a low pressure environment toward a surface of the sample. The electron beam thereby impinges on the sample at a target location, and thereby causes characteristic x-ray emission from the target location of the sample. A capping precursor is introduced into the low pressure environment, where the capping precursor forms a capping layer on the surface of the sample at the target location when contacted by the electron beam. The capping layer thereby reduces atom ejection from the sample at the target location, while not appreciably impeding and confounding the characteristic x-ray emission from the target location of the sample.

20 Claims, 1 Drawing Sheet

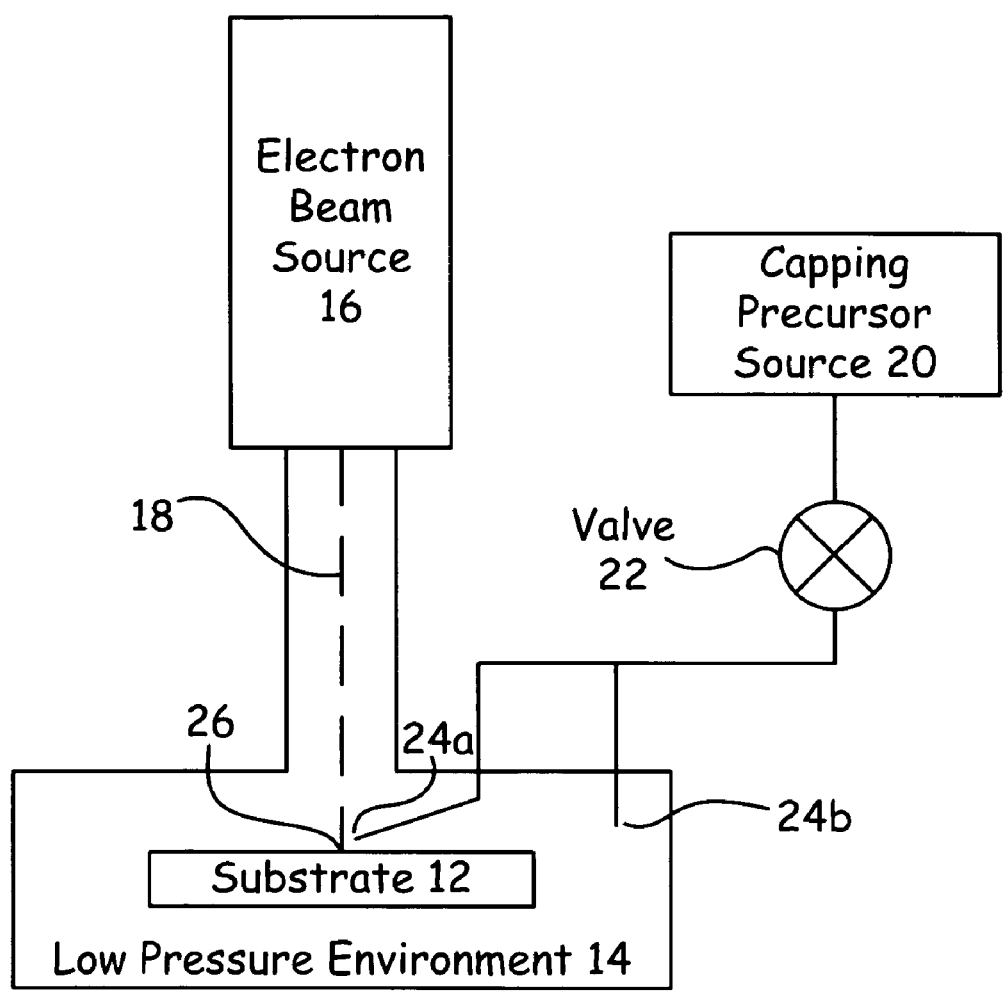

CAPPING LAYER TO IMPEDE ATOM EJECTION

FIELD

This invention relates to the field of integrated circuit fabrication. More particularly, this invention relates to electron beam stimulated x-ray analysis of integrated circuit layers.

BACKGROUND

Integrated circuit fabrication is typically accomplished by forming many different layers on a substrate. As the term is used herein, "integrated circuit" includes devices such as those formed on monolithic semiconducting substrates, such as those formed of group IV materials like silicon or germanium, or group III–V compounds like gallium arsenide, InP, or mixtures of such materials. The term includes all types of devices formed, such as memory and logic, and all designs of such devices, such as MOS and bipolar. The term also comprehends applications such as flat panel displays, solar cells, and charge coupled devices. Because the design tolerances of an integrated circuit are so strict, it is desirable to monitor the properties, such as thickness and elemental composition, of the various layers as they are formed. One way to measure the properties of film layers is to use a technique called electron stimulated x-ray metrology.

In very general terms, electron stimulated x-ray metrology works by directing a beam of electrons through a low pressure environment toward a sample surface. The electrons excite the atoms of the sample as they impinge against it. The excited atoms produce x-rays having properties that are characteristic of the properties of the sample, such as layer composition and layer thickness. Electron stimulated x-ray metrology is a highly favored technique, because in principle, it can be performed on production integrated circuits without damaging them.

Unfortunately, there are some problems with the technique. For example, deterioration of the x-ray signal over time, due to atom ejection, generally referred to as trending herein, requires that relatively short electron beam exposure times be used in order to get a reading that is closest to the initial value. However, a short acquisition time tends to result in a relatively large error bar spread. Thus, while repeated measurements at different points tend to result in a reduced precision, trending causes repeated measurements at the same point to result in a precision that is even further reduced.

What is needed, therefore, is a system that overcomes problems such as those described above, at least in part.

SUMMARY

The above and other needs are met by a method of reducing atom ejection from a sample during electron beam bombardment. An electron beam is directed through a low pressure environment toward a surface of the sample. The electron beam thereby impinges on the sample at a target location, and thereby causes characteristic x-ray emission from the target location of the sample. A capping precursor is introduced into the low pressure environment, where the capping precursor forms a capping layer on the surface of the sample at the target location when contacted by the electron beam. The capping layer thereby reduces atom ejection from the sample at the target location, while not appreciably impeding and confounding the characteristic x-ray emission from the target location of the sample.

In this manner, a capping layer is formed on the surface of the sample wherever the electron beam impinges on the sample. The capping layer reduces, and preferably eliminates the incidence of atom ejection from the sample, and thereby reduces and preferably eliminates the trending that is displayed when the electron beam impinges a given target location for an appreciable length of time. Because the trending is reduced, the readings taken using the method as described tend to be more exact. Thus, longer readings can be taken, and a higher precision in the results is attained.

In various embodiments according to this aspect of the invention, the method is implemented in an electron stimulated x-ray metrology system. Preferably, the capping layer substantially eliminates atom ejection from the sample at the target location. The capping precursor preferably includes at least one of alcohol, ketone, aldehyde, ether, ester, organic acid, organic halide, unsaturated organic molecule, organic molecule with a dipole that can form a weak bond, hydrogen bond, or van-der-Waals bond to the surface of the sample, silicon based halide, inorganic molecule capable of bonding to the surface of the sample, molecules with polar bonds such a carbon-halogen bond and silicon-halogen bond, dipoles such as unsaturated organic molecules, silicon based molecules such as $SiCl_4$. Most preferably the capping precursor includes a short chain hydrocarbon with an oxygen functional group, such as 2-propanol.

According to another aspect of the invention there is described an apparatus that directs electrons at a sample while reducing atom ejection from the sample. An electron beam source generates an electron beam and directs the electron beam toward the sample. A low pressure environment receives the electron beam from the electron beam source and encloses a target location on the sample. An injector receives a capping precursor and injects the capping precursor into the low pressure environment.

In various embodiments according to this aspect of the invention, the apparatus is implemented in an electron stimulated x-ray metrology system. A capping precursor source is preferably connected to the injector, and holds a store of the capping precursor. The injector may be a plurality of injectors. A flow rate adjustment is preferably connected to the injector, and adjusts a flow rate of the capping precursor. In one embodiment, the injector is disposed to inject the capping precursor at the target location. The capping layer preferably substantially eliminates atom ejection from the sample at the target location. The capping precursor preferably includes a short chain hydrocarbon and an oxygen functional group.

According to yet another aspect of the invention there is described an electron stimulated x-ray metrology system that directs an electron beam at a sample while reducing atom ejection from the sample. An electron beam source generates an electron beam and directs the electron beam toward the sample. A low pressure environment receives the electron beam from the electron beam source and encloses a target location on the sample. A capping precursor source holds a store of a capping precursor, and an injector disposed between the capping precursor source and the low pressure environment injects the capping precursor into the low pressure environment.

In various embodiments according to this aspect of the invention, the injector is a plurality of injectors. A flow rate adjustment is preferably connected to the capping precursor source, and adjusts a flow rate of the capping precursor into the low pressure environment. Preferably, the injector is disposed to inject the capping precursor at the target location. The capping layer preferably substantially eliminates atom ejection from the sample at the target location. The capping precursor most preferably includes a short chain hydrocarbon with an oxygen functional group.

BRIEF DESCRIPTION OF THE DRAWINGS

Further advantages of the invention are apparent by reference to the detailed description when considered in conjunction with the FIGURE, which is not to scale so as to more clearly show the details, wherein like reference numbers indicate like elements, and which depicts a functional block diagram of an apparatus according to a preferred embodiment of the invention.

DETAILED DESCRIPTION

With reference now to the FIGURE, there is depicted a functional block diagram of a system 10 according to a preferred embodiment of the present invention. The system 10 is preferably implanted as an electron stimulated x-ray metrology system, and thus includes the components and subsystems as are traditionally included with such a system, some of which are not depicted in the FIGURE so as to more completely focus attention on the more novel aspects of the system 10. The system 10 preferably includes an electron beam source 16 which directs an electron beam 18 toward a target location 26 on a substrate 12. Preferably, at least the electron beam 18 and the target location 26 of the substrate 12 are disposed within a low pressure environment 14.

A capping precursor source 20 preferably holds a store of a capping precursor, which has properties as described more completely below. The capping precursor is preferably introduced to the low pressure environment 14 through one or more injectors 24. As depicted in the FIGURE, injector 24a is disposed so as to introduce the capping precursor at a location within the low pressure environment 14 that is as close to the target location 26 on the substrate 12 as practical. Alternately, injector 24b is disposed so as to introduce the capping precursor at a more generalized location within the low pressure environment 14. The capping precursor is most preferably introduced as a gas into the low pressure environment 14.

While both or additional injectors 24 could be used, most preferably the injector 24a is used, so that a relatively smaller amount of the capping precursor is used, and the other components within the low pressure environment 14 are not exposed to the capping precursor to such a great extent. The amount of the capping precursor delivered to the low pressure environment 14 is preferably metered to some extent, such as through a valve 22.

The capping precursor is preferably a short chain hydrocarbon containing an oxygen functional group, such as 2-propanol. The capping precursor preferably contains a molecule that is broken up under the electron beam 18, and carbon atoms bond to the surface layer of the substrate 12, creating a capping layer that tends to impede the ejection of the atoms near the surface of the substrate 12. Because carbon is a relatively light element, thin layers of carbon do not significantly adversely affect the energy of the incoming electrons, nor do they absorb a significant amount of the emitted x-ray signal. Thus, the measurement capabilities of the system 10 are not significantly impeded by the capping layer that is formed on the substrate 12.

In this manner, the measurement duration can be greatly extended. In addition, signal precision is greatly enhanced. Thus, the measured value is still very close to the initial value, even after many minutes of measurement.

Other organic or inorganic molecules could also be used as the capping precursor, instead of 2-propanol or other carbon containing materials. The molecules that are most effective are preferably capable of van-der-Waals bonding or hydrogen bonding to the surface of the substrate 12. 2-propanol is a good example of a short chain hydrocarbon with a hydroxide group, and thus has the desired properties. Other molecules that contain an oxygen functional group such as a ketone (C=O), aldehyde (C=OH), organic acid (COOH), ester (COOR), or ether (COC), or possess other types of polar bonds such as carbon-halogen or silicon-halogen, or dipoles such as unsaturated organic molecules, that have a high sticking coefficient to the substrate 12 surface and acceptable volatility under the high vacuum conditions of the low pressure environment 14 may also serve well.

Silicon based molecules such as $SiCl_4$ or similar materials may have the added advantage of forming a silicon cap on the target location 26, which may be desirable for in-line gate process applications. In an alternate procedure, a pretreatment of the substrate 12 with the capping precursor, in either a liquid or a gaseous state, prior to bringing the substrate 12 into the low pressure environment, is followed by an electron beam 18 exposure on the target location 26 to form the capping layer.

The method and system 10 as described herein has proven to be a most effective method for obtaining stable, low-noise, x-ray signals for nitrogen and oxygen, such as in thin silicon oxynitride gate layers. The method and system 10 may also function for measurements of other films, such as aluminum oxide, or other layers that exhibit a signal that deteriorates, or trends, with exposure to an electron beam 18. The material of the capping precursor may be selected so as to be most compatible with the layer being measured, in addition to preferably exhibiting the other properties as described herein.

The foregoing description of preferred embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method of reducing atom ejection from a sample during electron beam bombardment, the method comprising the steps of:

directing an electron beam through a low pressure environment toward a surface of the sample, the electron beam thereby impinging on the sample at a target location and thereby causing characteristic x-ray emission from the target location of the sample, and introducing a capping precursor to the surface of the sample, where the capping precursor forms a capping layer on the surface of the sample at the target location when contacted by the electron beam, the capping layer thereby reducing atom ejection from the sample at the target location, while not appreciably impeding and confounding the characteristic x-ray emission from the target location of the sample.

2. The method of claim 1, wherein the method is implemented in an electron stimulated x-ray metrology system.

3. The method of claim 1, wherein the capping layer substantially eliminates atom ejection from the sample at the target location.

4. The method of claim 1, wherein the capping precursor includes at least one of alcohol, ketone, ether, ester, aldehyde, organic acid, organic halide, unsaturated organic molecule, organic molecule with a dipole that can form a weak bond, hydrogen bond, or van-der-Waals bond to the surface of the sample, silicon based halide, inorganic molecule capable of bonding to the surface of the sample, molecules with polar bonds such a carbon-halogen bond and silicon-halogen bond, dipoles such as unsaturated organic molecules, silicon based molecules such as $SiCl_4$.

5. The method of claim 1, wherein the capping precursor is a short chain hydrocarbon with an oxygen functional group.

6. The method of claim 1, wherein the capping precursor is 2-propanol.

7. An apparatus adapted to direct electrons at a sample while reducing atom ejection from the sample, the apparatus comprising:
 an electron beam source adapted to generate an electron beam and direct the electron beam toward the sample,
 a low pressure environment adapted to receive the electron beam from the electron beam source and to enclose a target location on the sample, and
 an injector adapted to receive a capping precursor and inject the capping precursor into the low pressure environment.

8. The apparatus of claim 7, wherein the apparatus is implemented in an electron stimulated x-ray metrology system.

9. The apparatus of claim 7, further comprising a capping precursor source connected to the injector and adapted to hold a store of the capping precursor.

10. The apparatus of claim 7, wherein the injector further comprises a plurality of injectors.

11. The apparatus of claim 7, further comprising a flow rate adjustment connected to the injector and adapted to adjust a flow rate of the capping precursor.

12. The apparatus of claim 7, wherein the injector is disposed to inject the capping precursor at the target location.

13. The apparatus of claim 7, wherein the capping layer substantially eliminates atom ejection from the sample at the target location.

14. The apparatus of claim 7, wherein the capping precursor includes a short chain hydrocarbon with an oxygen functional group.

15. An electron stimulated x-ray metrology system adapted to direct an electron beam at a sample while reducing atom ejection from the sample, the electron stimulated x-ray metrology system comprising:
 an electron beam source adapted to generate an electron beam and direct the electron beam toward the sample,
 a low pressure environment adapted to receive the electron beam from the electron beam source and to enclose a target location on the sample,
 a capping precursor source adapted to hold a store of a capping precursor, and
 an injector disposed between the capping precursor source and the low pressure environment and adapted to inject the capping precursor into the low pressure environment.

16. The apparatus of claim 15, wherein the injector further comprises a plurality of injectors.

17. The apparatus of claim 15, further comprising a flow rate adjustment connected to the capping precursor source and adapted to adjust a flow rate of the capping precursor into the low pressure environment.

18. The apparatus of claim 15, wherein the injector is disposed to inject the capping precursor at the target location.

19. The apparatus of claim 15, wherein the capping layer substantially eliminates atom ejection from the sample at the target location.

20. The apparatus of claim 15, wherein the capping precursor includes a short chain hydrocarbon with an oxygen functional group.

* * * * *